(12) United States Patent
Arora

(10) Patent No.: US 11,185,674 B2
(45) Date of Patent: Nov. 30, 2021

(54) TARGETED DELIVERY OF BIOLOGIC THERAPEUTIC AGENTS

(71) Applicant: Northwestern University, Evanston, IL (US)

(72) Inventor: Rishi Arora, Chicago, IL (US)

(73) Assignee: Northwestern University, Evanston, IL (US)

( * ) Notice: Subject to any disclaimer, the term of this patent is extended or adjusted under 35 U.S.C. 154(b) by 48 days.

(21) Appl. No.: 16/159,328

(22) Filed: Oct. 12, 2018

(65) Prior Publication Data

US 2019/0111241 A1 Apr. 18, 2019

Related U.S. Application Data

(60) Provisional application No. 62/571,492, filed on Oct. 12, 2017.

(51) Int. Cl.
| | | |
|---|---|---|
| *A61M 37/00* | (2006.01) | |
| *A61M 25/00* | (2006.01) | |
| *A61N 1/32* | (2006.01) | |
| *A61N 1/05* | (2006.01) | |
| *A61K 9/00* | (2006.01) | |

(52) U.S. Cl.
CPC ...... *A61M 37/0015* (2013.01); *A61M 25/003* (2013.01); *A61M 25/0082* (2013.01); *A61N 1/327* (2013.01); *A61K 9/0021* (2013.01); *A61M 37/0092* (2013.01); *A61M 2037/003* (2013.01); *A61M 2037/0023* (2013.01); *A61M 2037/0061* (2013.01); *A61N 1/05* (2013.01); *A61N 1/0502* (2013.01); *A61N 1/325* (2013.01)

(58) Field of Classification Search
CPC ...... A61M 37/0015; A61M 2037/0023; A61M 2037/003; A61M 2037/0038; A61M 2205/055; A61N 1/327; A61N 1/325; A61N 1/05; A61N 1/0502; A61N 1/0504
See application file for complete search history.

(56) References Cited

U.S. PATENT DOCUMENTS

| | | | |
|---|---|---|---|
| 5,445,148 A | 8/1995 | Jaraczewski et al. | |
| 6,256,533 B1 * | 7/2001 | Yuzhakov | A61M 37/0015 604/20 |

(Continued)

FOREIGN PATENT DOCUMENTS

WO WO 2019/075380 4/2019

OTHER PUBLICATIONS

Aistrup et al., Targeted nonviral gene-based inhibition of Galpha(i/o)-mediated vagal signaling in the posterior left atrium decreases vagal-induced atrial fibrillation. Heart Rhythm. 2011;8:1722-9.

(Continued)

*Primary Examiner* — Nilay J Shah
(74) *Attorney, Agent, or Firm* — Casimir Jones, S.C.; David W. Staple

(57) ABSTRACT

Medical devices comprising applicators that present a microneedle array and a separate electroporation array configured to simultaneously contact a tissue surface, a fluidic system connected to the microneedle array, and an electronic system connected to the electroporation array, for the coordinated delivery of a fluid biologic and electroporation energy to a tissue.

16 Claims, 9 Drawing Sheets

(56) References Cited

U.S. PATENT DOCUMENTS

| | | | | |
|---|---|---|---|---|
| 6,689,103 | B1* | 2/2004 | Palasis | A61B 17/3207 |
| | | | | 604/173 |
| 8,738,125 | B1* | 5/2014 | Heller | A61N 1/327 |
| | | | | 604/21 |
| 2004/0167458 | A1* | 8/2004 | Draghia-Akli | A61N 1/327 |
| | | | | 604/20 |
| 2006/0036209 | A1 | 2/2006 | Subramony et al. | |
| 2007/0060989 | A1 | 3/2007 | Deem et al. | |
| 2007/0242743 | A1* | 10/2007 | Scherman | A61N 1/306 |
| | | | | 375/238 |
| 2008/0009800 | A1* | 1/2008 | Nickel | A61M 37/0015 |
| | | | | 604/173 |
| 2011/0009807 | A1* | 1/2011 | Kjeken | A61N 1/327 |
| | | | | 604/21 |
| 2012/0197234 | A1* | 8/2012 | Sharma | A61M 25/0084 |
| | | | | 604/511 |
| 2015/0088050 | A1 | 3/2015 | Chang et al. | |

OTHER PUBLICATIONS

Balasubramaniam et al., AF and Heart failure: the chicken or the egg? Heart. 2009;95:535-539.

Benjamin et al., Independent risk factors for atrial fibrillation in a population-based cohort. The Framingham Heart Study. JAMA. 1994;271:840-4.

Calkins et al., 2012 HRS/EHRA/ECAS Expert Consensus Statement on Catheter and Surgical Ablation of Atrial Fibrillation: recommendations for patient selection, procedural techniques, patient management and follow-up, definitions, endpoints, and research trial design. Europace. 2012;14:528-606.

Dean, Nonviral gene transfer to skeletal, smooth, and cardiac muscle in living animals. Am J Physiol Cell Physiol. 2005;289:C233-45.

Feinberg et al., Prevalence, age distribution, and gender of patients with atrial fibrillation. Analysis and implications. Archives of Internal Medicine. 1995;155:469-73.

Gerstenfeld et al., Predictors of success after selective pulmonary vein isolation of arrhythmogenic pulmonary veins for treatment of atrial fibrillation. Heart Rhythm. 2006;3:165-70.

Greener et al., Gene therapy strategies for cardiac electrical dysfunction. J Mol Cell Cardiol. 2011;50:759-65.

Jeong et al., Metabolic stress, reactive oxygen species, and arrhythmia. J Mol Cell Cardiol. 2012;52:454-63.

Korantzopoulos et al., The role of oxidative stress in the pathogenesis and perpetuation of atrial fibrillation. Int J Cardiol. 2007;115:135-43.

Lakshminarayan et al., Clinical epidemiology of atrial fibrillation and related cerebrovascular events in the United States. Neurologist. 2008;14:143-50.

Ling et al., Comorbidity of atrial fibrillation and heart failure. Nat Rev Cardiol. 2016;13:131-47.

Lip et al., Atrial fibrillation—the growing epidemic. Heart. 2007;93:542-3.

Pappone et al., Atrio-esophageal fistula as a complication of percutaneous transcatheter ablation of atrial fibrillation. Circulation. 2004;109:2724-6.

Rincon et al., Gene therapy for cardiovascular disease: advances in vector development, targeting, and delivery for clinical translation. Cardiovasc Res. 2015;108:4-20.

Rodrigues et al., Left atrial function after ablation for paroxysmal atrial fibrillation. American Journal of Cardiology. 2009;103:395-8.

Su et al., Nonviral gene therapy targeting cardiovascular system. Am J Physiol Heart Circ Physiol. 2012;303:H629-38.

Tevaearai et al., In vivo electroporation-mediated gene delivery to the beating heart. Methods Mol Biol. 2014;1121:223-9.

Verma et al., Efficacy of adjuvant anterior left atrial ablation during intracardiac echocardiography-guided pulmonary vein antrum isolation for atrial fibrillation. J Cardiovasc Electrophysiol. 2007;18:151-6.

Youn et al., Oxidative stress in atrial fibrillation: an emerging role of NADPH oxidase. J Mol Cell Cardiol. 2013;62:72-9.

International Search Report and Written Opinion for PCT/US2018/055684, dated Dec. 13, 2018, 13 pages.

* cited by examiner

A. PCR

B. Western blot

US 11,185,674 B2

TARGETED DELIVERY OF BIOLOGIC THERAPEUTIC AGENTS

CROSS-REFERENCE TO RELATED APPLICATIONS

The present invention claims the priority benefit of U.S. Provisional Patent Application 62/571,492, filed Oct. 12, 2017, which is incorporated by reference in its entirety.

FIELD

Provided herein are medical devices for the targeted delivery of biologic therapeutic agents.

BACKGROUND

One of the greatest obstacles to successful gene therapy is the ability to achieve adequate gene transfer into the cells of diseased tissue. The use of viral vectors has been associated with off-target effects and inadequate gene transfer leading to the development of non-viral approaches.

SUMMARY

Provided herein are medical devices for the targeted delivery of biologic therapeutic agents. In some embodiments, provided herein are medical devices capable of (1) uniformly injecting a biologic (e.g., nucleic acid) and (2) delivering reversible electroporation. In some embodiments, the devices herein facilitate effective, homogeneous and reproducible gene expression in targeted cells. In some embodiments, devices comprise a micro-fluidic system incorporating hollow microneedles combined with a multi-electrode electroporation array in a single, integrated applicator. This applicator provides the capability to inject a therapeutic agent uniformly into the surface of an organ (e.g., a large surface area of organ tissue) followed by the application of reversible electroporation through several electrodes simultaneously to facilitate effective gene transfer uniformly within the same tissue. In some embodiments, the devices herein facilitate biologic delivery to any suitable organ, such as the heart (e.g., atria), liver, kidney, pancreas, skin, lung, prostate, uterus, ovaries, etc.

Targeted delivery of biologic therapeutic agents using the devices herein finds use in the treatment of a variety of disease conditions including atrial and ventricular arrhythmias, congestive heart failure, cirrhosis, renal disease, cancer, etc.

The devices and methods herein provide delivery of a therapeutic nucleic acid, followed by gene expression localized to the treatment site providing a more effective and safer gene delivery method, particularly compared to the use of viral vectors which are associated with inadequate gene transfer and off-target effects. In some embodiments, the devices and methods herein facilitate gene transfer without a viral vector.

In some embodiments, devices and methods are provided for the physical delivery of genes (non-viral) into larger areas of internal organ tissue in an efficient, effective, uniform, homogenous, and reproducible manner. In some embodiments, devices herein combine the uniform injection of a biologic (e.g., nucleic acid) using a microfluidic system with reversible multi-electrode electroporation in a single delivery applicator capable of uniformly treating a larger area (e.g., 0.2 $cm^2$, 0.4 $cm^2$, 0.6 $cm^2$, 0.8 $cm^2$, 1.0 $cm^2$, 1.5 $cm^2$, 2.0 $cm^2$, 2.5 $cm^2$, 3.0 $cm^2$, 3.5 $cm^2$, 4.0 $cm^2$, 4.5 $cm^2$, 5.0 $cm^2$, 6.0 $cm^2$, 7.0 $cm^2$, 8.0 $cm^2$, 9.0 $cm^2$, 10 $cm^2$, 12 $cm^2$, 14 $cm^2$, 16 $cm^2$, 18 $cm^2$, 20 $cm^2$, or more, or ranges therebetween) of organ tissue in a single, reproducible application.

In some embodiments, provided herein are medical devices comprising a micro-fluidic system incorporating hollow microneedles. In some embodiments, devices additionally comprise a multi-electrode electroporation array. In some embodiments, a single device is provided comprising a microfluidic delivery system (e.g., comprising multiple microneedles) and an electroporation array.

In some embodiments, a biologic delivery device comprises multiple hollow microneedles (e.g., connected to a micro-fluidic system) that facilitate homogeneous gene injection over an exposed surface of the organ tissue. FIG. 1 shows a schematic of a microneedle array that allows injection of a biological therapeutic into an organ or tissue (e.g., epicardium of the atrium). In some embodiments, technical considerations for the device include the biomaterial for injection (e.g., nucleic acid, particular gene, etc.), needle size, array size, and spacing pitch. Materials used to construct the hollow microneedles may be metallic (e.g. stainless steel) or non-metallic (e.g. silicone). Microneedle size may be 1-2 mm thick or larger injecting to a depth of 0.5-1.5 mm designed to minimize the risk of organ damage, yet large enough to inject DNA through these microneedles without risking DNA shearing. In some embodiments, the applicator comprises a flexible material and sized to allow a greater treatment area of organ tissue for each application. In some embodiments, the device provides homogeneous coverage of organ tissue using optimal spacing between injection needles (e.g., 0.5-2 mm).

FIG. 2 shows an exemplary electroporation applicator that provides uniform electroporation over a large tissue (e.g., atrial) surface. In some embodiments, the gene delivery device comprises multiple electroporation electrodes (e.g., with 1 cm inter-electrode spacing) built into the flexible applicator to facilitate simultaneous and uniform electroporation of the organ tissue following the gene injection.

In some embodiments, a gene delivery device integrates microfluidic injection with uniform reversible electroporation in a single applicator. In some embodiments, the microneedles and electroporation electrodes described herein are mounted on a flexible applicator of a desired size (e.g. 8×2 cm). FIG. 3 represents an exemplary design incorporating microneedles and the electroporation electrodes on a flexible 8×2 cm applicator. This design allows uniform (homogeneous) gene injection and electroporation through the same device over a wide surface area of the organ. In some embodiments, the integrated gene delivery device combining microfluidic injection with uniform reversible electroporation is customizable for the target delivery of biologic therapeutic agents to organ systems including the heart, liver, kidney, etc., for the treatment of a variety of disease conditions including atrial and ventricular arrhythmias, congestive heart failure, cirrhosis, and renal disease. In some embodiments, customization includes the optimal injection and electroporation parameters to allow robust and homogeneous gene transfer with the delivery device for the application without causing toxicity in the organ.

In some embodiments, provided herein are devices comprising: (a) an applicator that presents (i) a microneedle array, and (ii) an electroporation array for contacting a tissue surface; (b) a fluidic system connected to the microneedle array for simultaneous and uniform delivery of a fluid biologic to the tissue; and (c) an electronic system connected to the electroporation array for coordinated delivery of electroporation energy from the electroporation array to the tissue. In some embodiments, the applicator is located at the distal end of a catheter. In some embodiments, the microneedle array comprises 4 to 200 microneedles (e.g., 4, 6, 8, 10, 15, 20, 25, 30, 35, 40, 45, 50, 60, 70, 80, 90, 100, 125, 150, 175, 200, or ranges therebetween). In some embodiments, the electroporation array comprises 4 to 200 electrodes (e.g., 4, 6, 8, 10, 15, 20, 25, 30, 35, 40, 45, 50, 60, 70, 80, 90, 100, 125, 150, 175, 200, or ranges therebetween). In some embodiments, the applicator is flexible to facilitate contact of all microneedles of the microneedle array and all electrodes of the electroporation array against the tissue. In some embodiments, the applicator covers a portion of the tissue that is 2-20 $cm^2$ (e.g., 2 $cm^2$, 3 $cm^2$, 4 $cm^2$, 5 $cm^2$, 6 $cm^2$, 7 $cm^2$, 8 $cm^2$, 9 $cm^2$, 10 $cm^2$, 11 $cm^2$, 12 $cm^2$, 13 $cm^2$, 14 $cm^2$, 15 $cm^2$, 16 $cm^2$, 17 $cm^2$, 18 $cm^2$, 19 $cm^2$, 20 $cm^2$, or ranges therebetween). In some embodiments, there is 0.1 to 1.0 mm (e.g., 0.1 mm, 0.2 mm, 0.5 mm, 0.75 mm, 1.0 mm, or ranges therebetween) between adjacent microneedles of the microneedle array. In some embodiments, there is 0.1 to 1.0 mm (e.g., 0.1 mm, 0.2 mm, 0.5 mm, 0.75 mm, 1.0 mm, or ranges therebetween) between adjacent electrodes of the electroporation array. In some embodiments, the electronic system comprises an electroporation controller and an electroporation generator. In some embodiments, when the applicator is in proper contact with the tissue, the microneedles are at angle between 5° and 90° (perpendicular) to the surface of the tissue. In some embodiments, when the applicator is in proper contact with the tissue, the microneedles are at 5°, 10°, 15°, 20°, 25°, 30°, 35°, 40°, 45°, 50°, 55°, 60°, 65°, 70°, 75°, 80°, 85°, 90°, or ranges therebetween). In some embodiments, the electronic system comprises an electroporation controller and an electroporation generator. In some embodiments, the electroporation controller activates all or a subset of the electrodes in the electroporation array according to a programmed schedule.

In some embodiments, provided herein are methods of delivering a biologic agent to a tissue, comprising: (a) placing the applicator of a device herein against the tissue; (b) injecting the biologic agent into the tissue via the fluidic system and microneedle array; and (c) electroporating the tissue with the electroporation array. In some embodiments, the tissue is cardiac tissue. In some embodiments, the tissue comprises epicardial tissue. In some embodiments, the tissue comprises endocardial tissue. In some embodiments, electroporation by all or a subset of the electrodes in the electroporation array is coordinated with delivery of the biologic agent into the tissue by all or a subset of the microneedles of the microneedle array. In some embodiments, electrodes adjacent to a microneedle or set of microneedles are energized in a coordinated manner with delivery of the biologic agent by the microneedle or set of microneedles. In some embodiments, the electrodes adjacent to a microneedle or set of microneedles are energized immediately before, during, and/or immediately after delivery of the biologic agent by the microneedle or set of microneedles. In some embodiments, different sets of microneedles and electrodes are utilized at different times in a treatment course.

DETAILED DESCRIPTION

Figure 1:
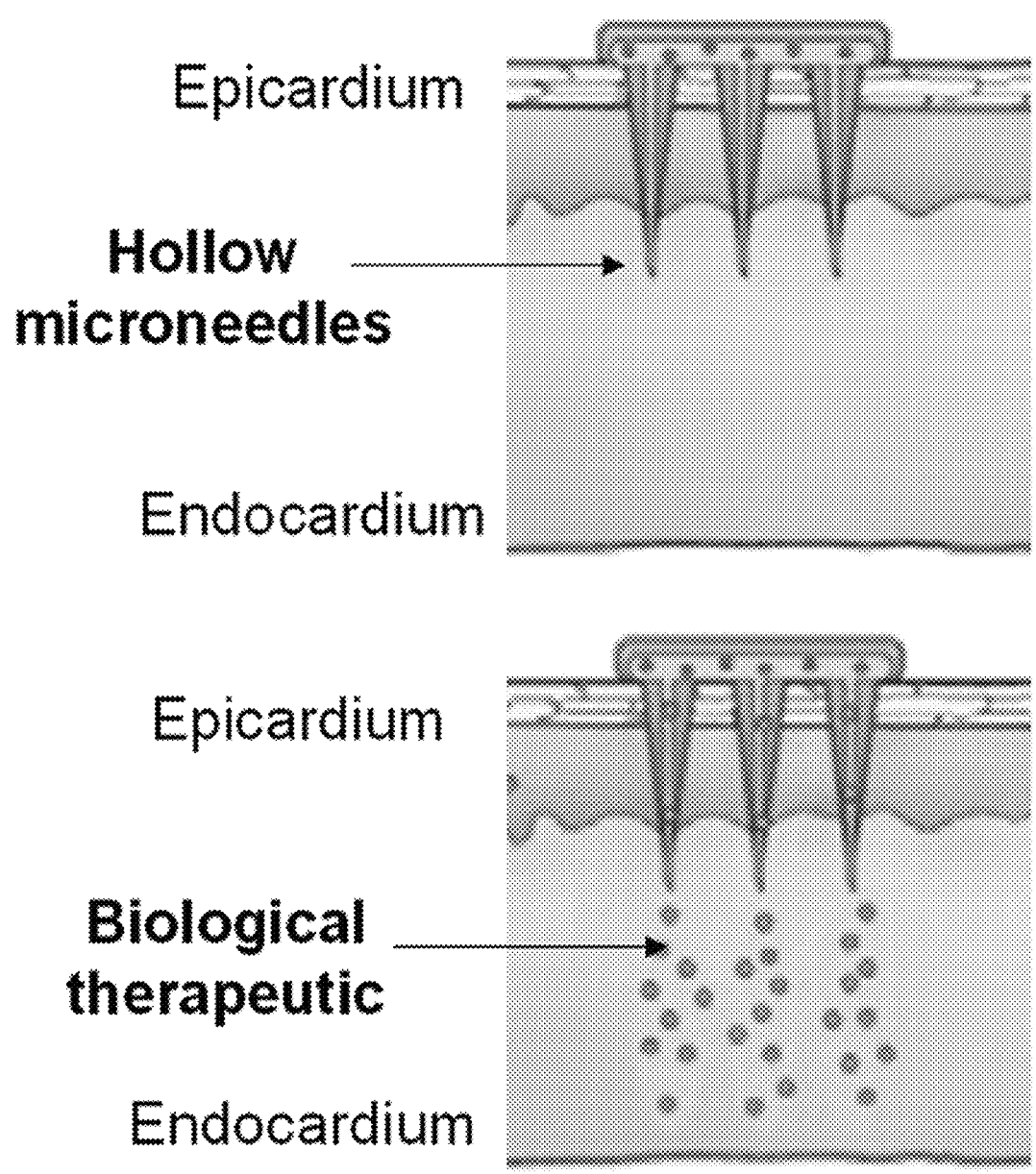
FIG. 1. Exemplary hollow microneedles for injecting a biological therapeutic in tissue (e.g., the atrium via an epicardial approach).

Atrial fibrillation (AF) is the most common heart rhythm disorder. It affects >3 million Americans and is a major cause of stroke. Since AF is primarily an age-related disease, it is fast becoming an epidemic in an aging population. Unfortunately, current therapies for AF—both pharmacological and ablation-based—are sub-optimal in patients with persistent AF. This is thought to be in part because current treatments do not target the fundamental, molecular mechanisms that cause AF.

In some embodiments, provided herein is an approach to AF treatment that targets one or more molecular mechanisms underlying development of the AF disease state. In some embodiments, the devices and methods herein target two fundamental mechanisms that contribute to electrical remodeling in AF, oxidative stress (OS) and parasympathetic nervous system signaling. In some embodiments, devices and methods herein target the underlying mechanisms of AF via delivery of a biologic agent. In certain embodiments, devices and methods herein target the underlying mechanisms of AF via delivery of a nucleic acid. In particular embodiments, devices and methods herein target the underlying mechanisms of AF via delivery of a nucleic acid gene therapy agent.

An obstacle to successful gene therapy, particularly in the heart, is the ability to achieve adequate gene transfer, for example, in cardiac myocytes (Ref 17; incorporated by reference in its entirety). Recent years have seen advances in the development and optimization of physical methods such as electroporation and sonoporation to achieve gene delivery in the heart and in other organ systems (Ref. 18; incorporated by reference in its entirety). Even with viruses—which can successfully cross the cardiac cell membrane—gene transfer into cardiomyocytes is significantly improved with electroporation (Ref. 19; incorporated by reference in its entirety). Since viruses have significant potential for off-target effects (Ref 20; incorporated by reference in its entirety), there may, in some embodiments, be advantages to using naked DNA (e.g., plasmids) for gene therapy, if there is another mechanism of efficiently delivering the DNA into cells.

In some embodiments, provided herein are devices and methods for the targeted delivery of biologics (e.g., nucleic acids, gene therapy agents, etc.) to, for example, the epicardium for the treatment of, for example, atrial fibrillation. In some embodiments, the devices herein encompass microneedle-based injection and electroporation technologies (e.g., array-based electroporation) for a precise and targeted delivery of biologics into the tissue (e.g., epicardium, etc.). In some embodiments, the devices are capable of delivering multiple biologics (e.g., nucleic acids (e.g., trans-genes)) into, for example, the atrium in a precise amount so that potential toxicities are avoided.

Experiments were conducted during development of embodiments herein using a syringe to inject gene plasmid followed by electroporation using a commercially available set of bipolar electrodes for research laboratory use. While these electrodes allow adequate atrial gene transfer (Ref. 12; incorporated by reference in its entirety), the electrode design necessitates that injection and electroporation be performed sequentially at several sites in each atrium, making gene delivery time-consuming, cumbersome, and subject to considerable user variability.

To facilitate more homogeneous and reproducible gene expression in the atrium regardless of user, provided herein are electroporation applicators with one or more of the following characteristics: (a) a micro-electrode array attached to a micro-fluidic system, that facilitates homogeneous injection of a biological therapeutic in the atrium, and (b) a multi-electrode array that facilitates simultaneous electroporation through several electrodes at one time, thereby allowing uniform electroporation over a large atrial surface area.

In some embodiments, the gene delivery devices described herein dramatically simplify epicardial gene delivery and allow early adoption of an AF gene therapy by cardiac surgeons. The devices herein may also find use in endocardial (trans-venous) gene therapy for AF. The gene delivery devices herein have utility for gene delivery in the atrium (for AF), but also for the delivery of biological agents in the ventricle (e.g. for congestive heart failure, ventricular arrhythmias), as well as outside the heart in other organs (e.g. liver, kidney). In some embodiments, the devices described herein are not limited to use in any one organ or tissue, for the treatment of any one disease of condition, or for the delivery of any one type of biologic. Embodiments described herein for the atrial delivery of nucleic acid gene therapy agents for the treatment of AF should also be viewed as useful for other organs and tissues, for the delivery of other biologic agents, and for the treatment of other disease and conditions.

Experiments conducted during development of embodiments herein to identify trans-genes to target key molecular mechanisms underlying AF. Fundamental mechanisms in the creation of the atrial fibrillation (AF) disease state and several trans-genes that selectively target these mechanisms in the atrium have been identified (Ref. 14-16; incorporated by reference in their entireties). In some embodiments, devices and methods herein target, either singly or in combination, two fundamental mechanisms that contribute to electrical remodeling in AF, oxidative stress and parasympathetic nervous system signaling. In some embodiments, nucleic acids (e.g., plasmids) expressing the following trans-genes are used: NOX2 shRNA (this transgene inhibits NOX2, a major enzymatic source of oxidative stress), and C-terminal Gαi+Gαo inhibitory peptides (e.g., at a 1:1 ratio) (these plasmids inhibit parasympathetic signaling in the atrium). In some embodiments, a subject is administered a biological product comprising a combination of NOX2 shRNA+Gαi expressing plasmid+Gαo expressing plasmid.

In some embodiments, devices and methods herein utilize electroporation to achieve gene delivery in tissues (e.g., the atrium). One obstacle to successful gene therapy in the heart is the ability to achieve adequate gene transfer in cardiac myocytes (Ref 17; incorporated by reference in its entirety). Both viral and non-viral vectors have been used for cardiac gene delivery. The potential advantages of viruses are long term gene expression (e.g. using AAV) (Refs. 58,59; incorporated by reference in their entireties) and less need for a physical method (e.g. electroporation, sonoporation) to facilitate gene delivery. However, viral vectors have potential for off-target effects. In recent years, there have been significant advances in non-viral delivery approaches, including: longer acting promoters, tissue specific enhancers, and optimization of physical methods such as electro or sonoporation to facilitate gene delivery. Use of a physical method nearly eliminates the possibility of off-target effects, as gene expression is localized to the site of electro/sonoporation. Plasmid DNA is rapidly degraded in blood and has no mechanism to transfect other cells after IV injection. In some embodiments, these advantages also obviate the need for organ- or tissue-specific promoters (e.g., cardiac specific). Furthermore, a physical method such as electroporation appears to significantly enhance even viral gene transfection (e.g., in the atrium) (Refs. 11,60; incorporated by reference in their entireties). In some embodiments, devices and methods herein utilize electroporation-facilitated non-viral biologic (e.g., nucleic acid (e.g., trans-gene)) delivery.

Experiments were conducted during development of embodiments herein using gene injection+electroporation in canine models of AF which demonstrate that transgenes (plasmids) are successfully expressed in the atrium by using electroporation, with a resulting decrease in AF in two clinically relevant large animal models of AF.

Figure 2:
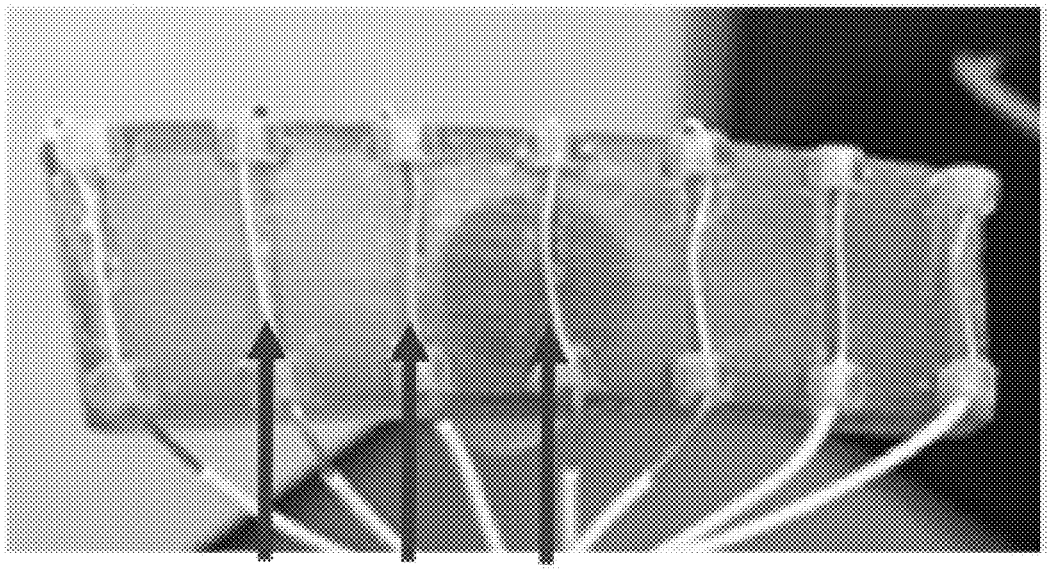
FIG. 2. Exemplary electroporation applicator.
Figure 3:
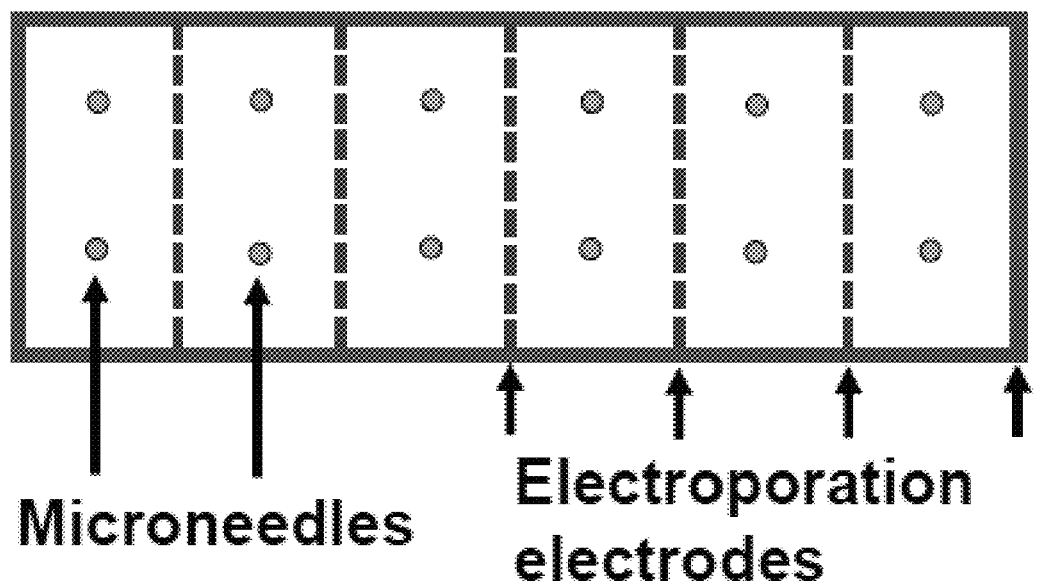
FIG. 3. Microneedles and electroporation electrodes combined into one applicator.
Figure 4:
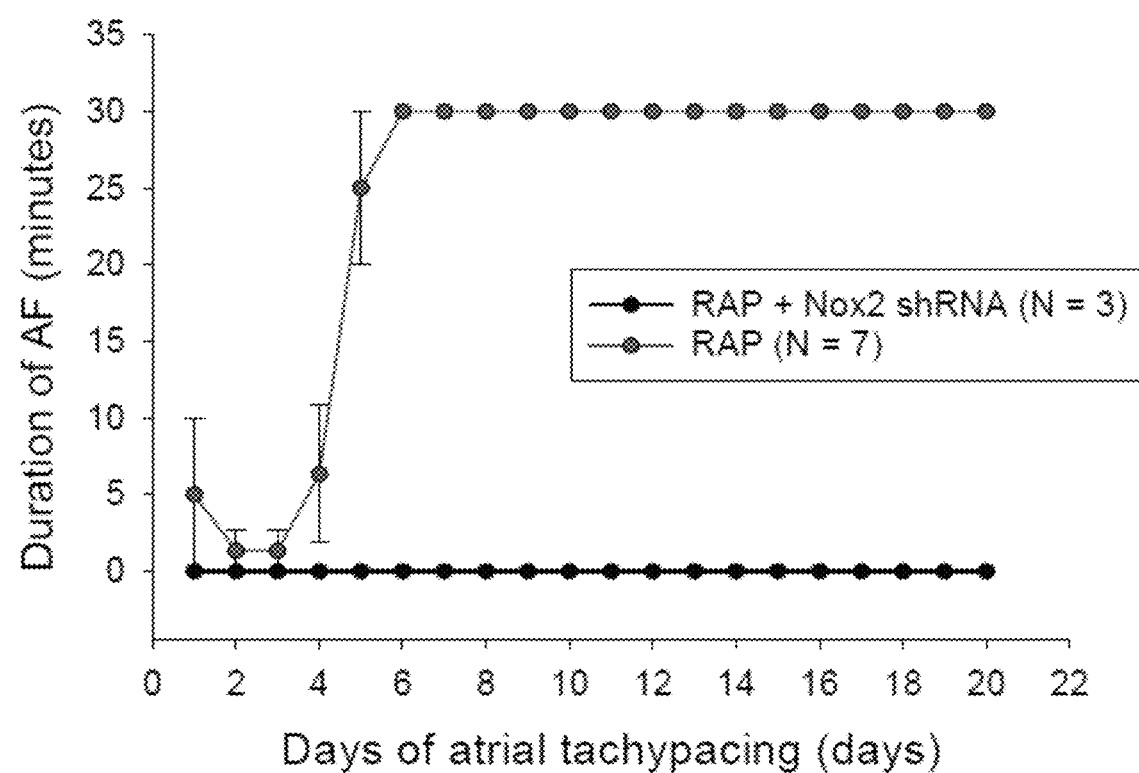
FIG. 4. NOX2 shRNA prevents AF in RAP. Dogs were injected with NOX2 shRNA or no/scrambled gene, followed by 3 weeks of ATR.
Figure 5:
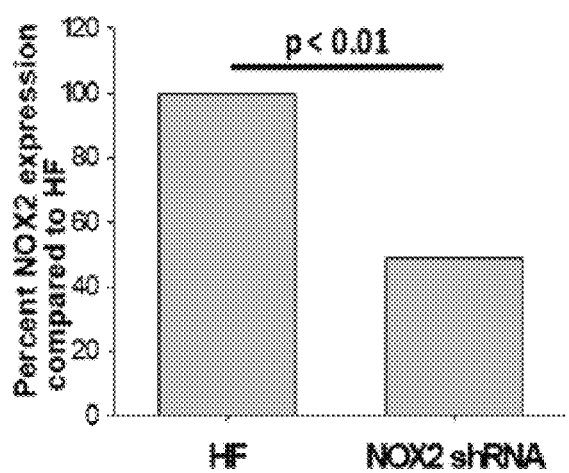
FIG. 5, Panels A and B. Decrease in native NOX2 expression in atrial transfected with NOX2 shRNA.
Figure 5:
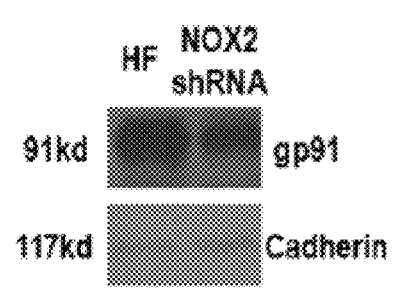

Experiments were conducted during development of embodiments herein to determine whether chronic expression of NOX2 shRNA in the left atrium prevents RAP induced ERP shortening and AF. It was hypothesized that chronic NOX2 knockdown in the PLA by NOX2 shRNA will attenuate RAP induced ERP shortening. In 3 animals, 10 mg of plasmid expressing NOX2 shRNA was injected sub-epicardially in the PLA. 7 control animals were also subjected to RAP (one injected with scrambled gene, one sham control, others subjected to RAP without being subjected to thoracotomy). One week after gene injection, all animals were subjected to RAP at 600 bpm (without AV node ablation) for 20 days. Every 48 hours, pacing was stopped for 30-60 minutes to assess for spontaneous AF (defined as AF that did not terminate during this period). As depicted in FIG. 4, the control dogs developed sustained AF after 6 days of RAP. In contrast, no significant AF was noted in NOX2 shRNA animals (NOX2 shRNA vs controls, $p<0.01$, log rank test; FIG. 2). ERPs were markedly longer in NOX2 shRNA dogs vs controls ($124\pm25$ vs $<50$ msec; $p<0.05$). These experiments demonstrate that NOX2 inhibition prevents RAP induced ERP shortening, with a resulting inhibition of AF onset. NOX2 is key to creation of electrical remodeling in RAP.

Experiments were conducted during development of embodiments herein to demonstrate that chronic NOX2 shRNA expression in the PLA improves conduction, prevents atrial fibrosis and decreases AF in HF. In 3 animals, 5 mg of NOX2 shRNA (under control of the RNA polymerase III promoter, U6) was injected sub-epicardially in the PLA, followed by electroporation. 5 animals underwent injection of pUBc-LacZ (i.e. HF controls). Ventricular tachypacing was then performed at 240 bpm for 3 weeks, followed by open-chest mapping. LA was examined for NOX2 knockdown (PCR, western blot) and % fibrosis.

Figure 6:
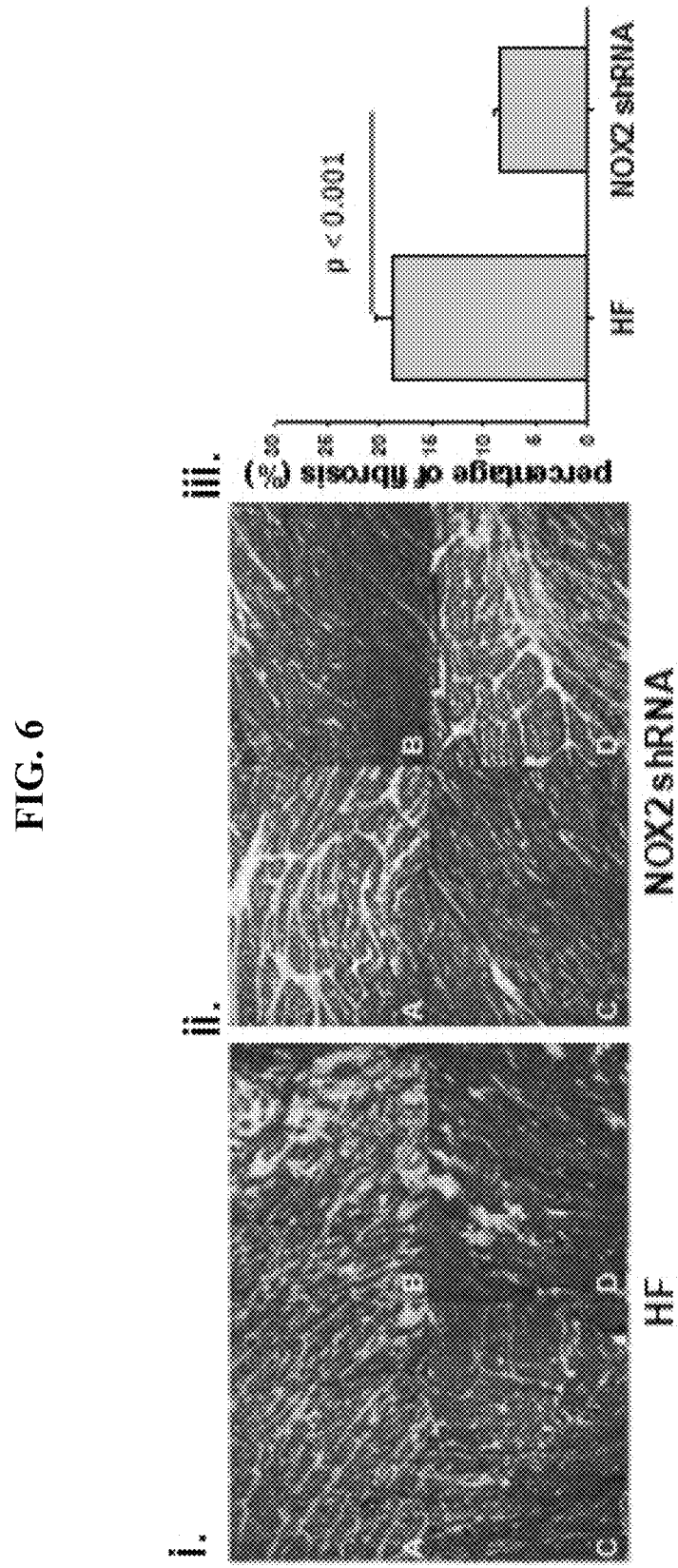
FIG. 6. NOX2 shRNA prevents fibrosis in HF PLA. Panel i shows PLA from a HF dog that did not receive gene. ii shows PLA from a HF dog injected with NOX2 shRNA. Fibrosis is stained (arrows). iii shows % fibrosis was significantly decreased with NOX2 shRNA.

AF duration was significantly decreased by NOX2 shRNA (NOX2 shRNA vs LacZ=636±151 vs 6±0.6 seconds; p<0.01). There was >50% knockdown of native NOX2 in PLA of NOX2 shRNA vs LacZ dogs (FIG. 2). FIG. 6 shows that fibrosis was significantly decreased in NOX2 shRNA vs LacZ injected PLA. Ox-CaMKII expression was also reduced with NOX2 shRNA. These data demonstrate that NOX2 shRNA reduces atrial fibrosis in HF (and thereby result in a decrease in inducible AF).

Figure 7:
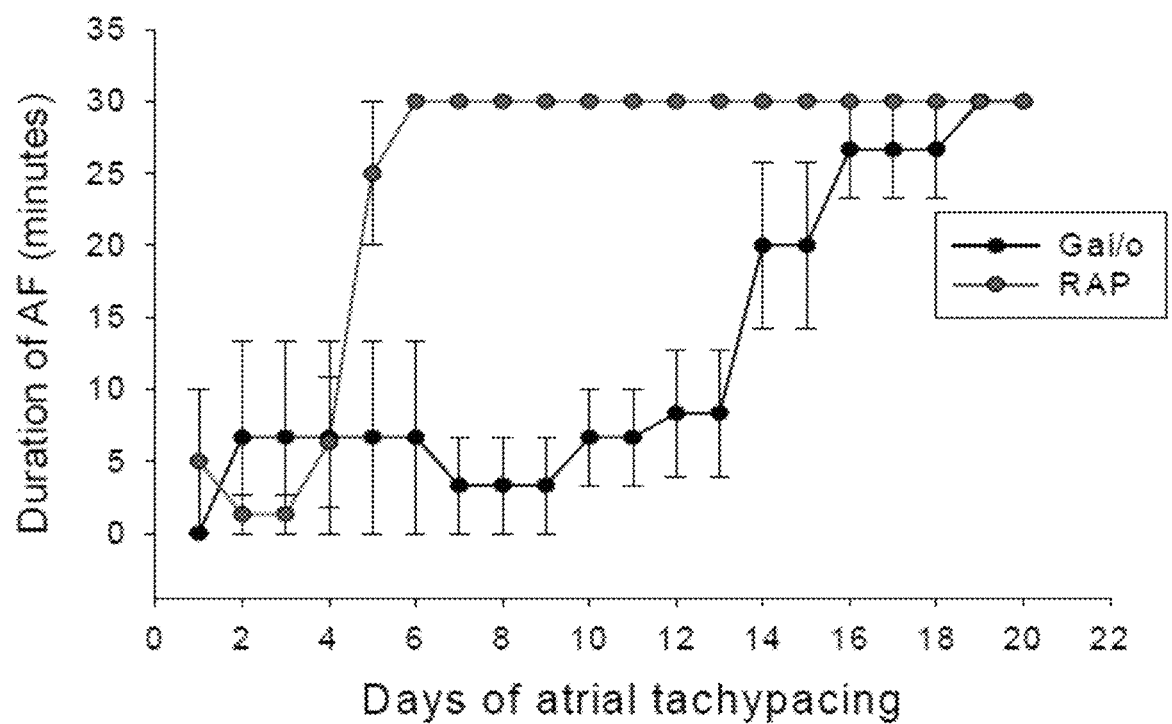
FIG. 7. $G\alpha_{i/o}$ expressing minigene delays time to AF onset in ATR. Dogs were injected with NOX2 shRNA or with no gene (or scrambled gene), followed by 3 weeks of ATR.

Experiments were conducted during development of embodiments herein to demonstrate that minigenes expressing Gαi/o inhibitory peptides (Gαi/o-ct) attenuate ERP shortening and AF in RAP. There is pronounced autonomic nerve remodeling—specifically parasympathetic nerve sprouting—in the setting of RAP. Parasympathetic nerves— via Gαi/o signaling—are known to cause significant effective refractory period (ERP) shortening in the atrium, with resulting substrate for AF. Therefore, experiments were conducted to target disruption of parasympathetic nerve signaling by inhibiting Gαi2+Gαo1 signaling to attenuate RAP induced ERP shortening and resulting AF. 10 mg of plasmid expressing Gαi2+Gαo1 peptide (under control of a long acting UBc promoter) was injected in the PLA in 3 dogs. 5 control animals were also subjected to RAP (one injected with scrambled gene, one sham control, the other controls underwent RAP without a thoracotomy). All animals then underwent RAP at 600 bpm (without AV node ablation) for 20 days. Every 48 hours, pacing was stopped for 30-60 minutes to assess for sustained AF. FIG. 7 shows that Gαi/o-ct results in a significant delay in AF onset in RAP dogs (p<0.05). This was accompanied by significant ERP prolongation (93±13 in Gαi/o vs<50 msec in controls; p<0.05). These data indicate that remodeled parasympathetic nerves contribute to ERP shortening and AF in RAP.

Figure 8:
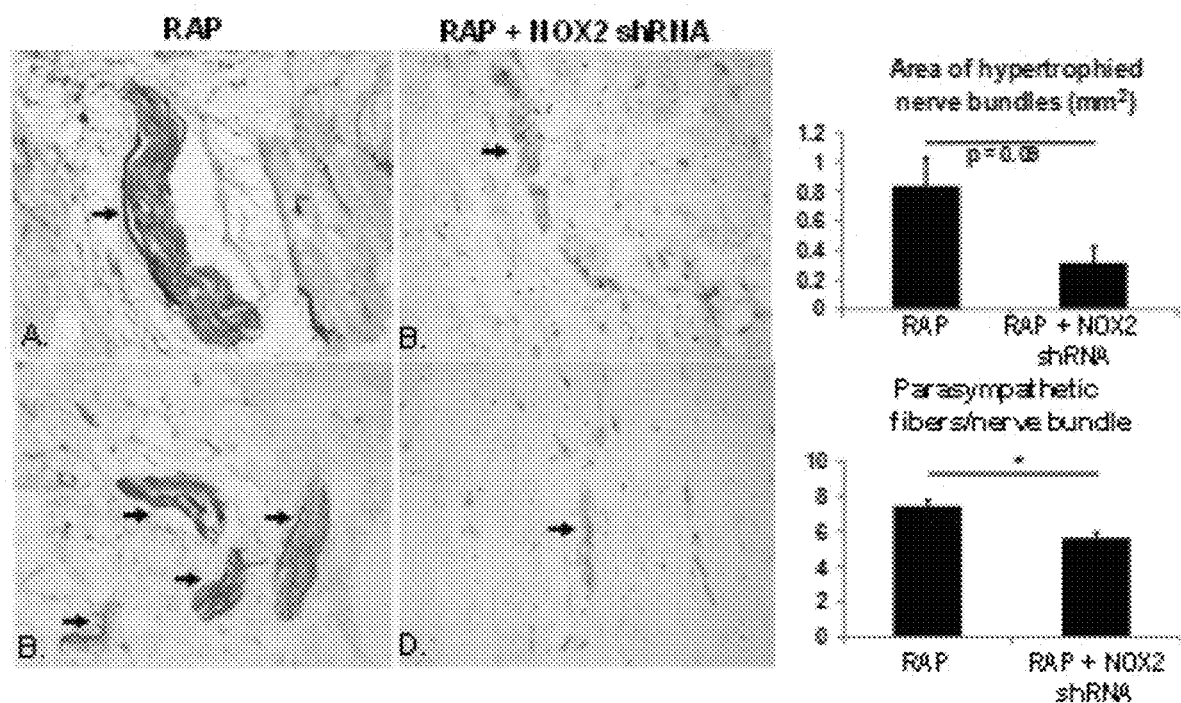
FIG. 8. NOX2 shRNA prevents neural hypertrophy and parasympathetic nerve sprouting in RAP.

Experiments were conducted during development of embodiments herein to demonstrate synergy between NOX2 shRNA and Gαi/o inhibitory peptides in decreasing AF in RAP model. Experiments indicate that a combination of NOX2 shRNA and Gαi/o inhibitory peptides are more effective at reducing electrical remodeling in AF that either trans-gene alone. The reason is that oxidative stress appears to be intricately involved in autonomic nerve remodeling in the atrium in the setting of AF. As shown in FIG. 8, dogs receiving NOX2 shRNA demonstrate a significant decrease in parasympathetic nerve sprouting, compared to dogs that did not receive the gene. This prevention of nerve growth is accompanied by significant attenuation of ERP shortening in these dogs, with a resulting absence of AF (FIG. 4). These data implicate oxidative stress in the creation of autonomic remodeling (nerve growth) in the atrium. Prevention of this autonomic hyperinnervation is a mechanism by which NOX2 shRNA prevents electrical remodeling in the RAP model; although an understanding of the mechanism is not necessary to practice the invention herein. The gene combination, by inhibiting both structural and functional aspects of neural remodeling, is more effective—and synergistic— in reducing electrical remodeling in AF than either gene alone.

Figure 9:
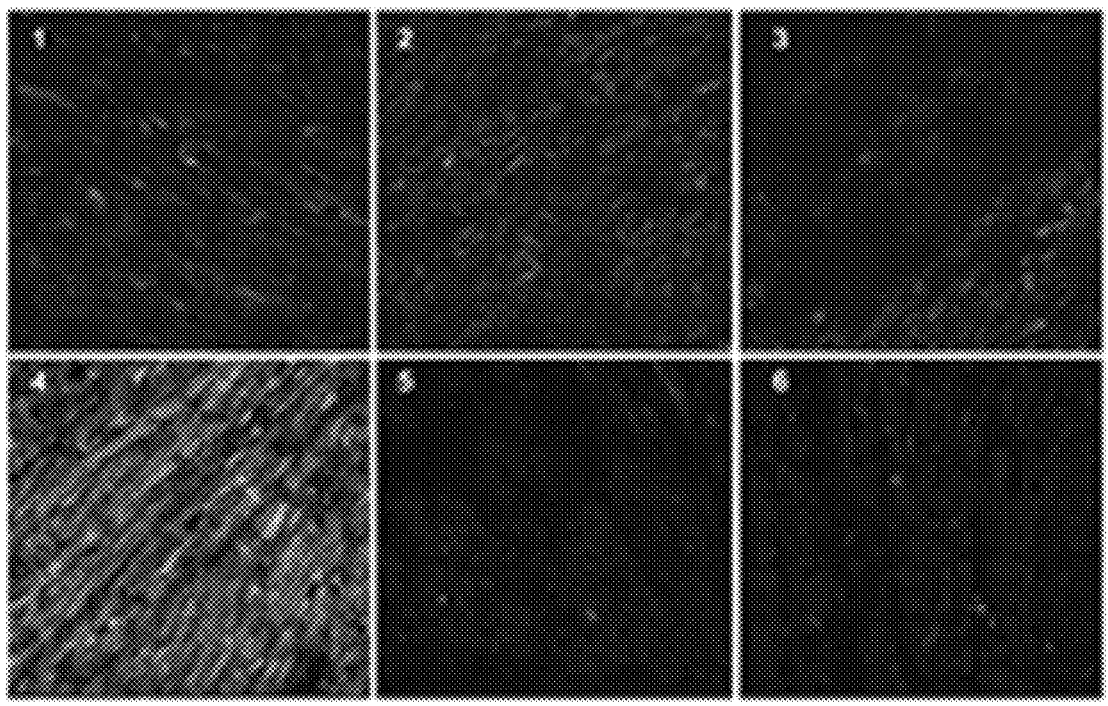
FIG. 9. Electroporation leads to gene expression in the atrium.

Experiments conducted during development of embodiments herein demonstrate that currently available electroporation techniques lead to heterogeneous gene expression in tissue (e.g., atrium). FIG. 9 shows that electroporation leads to gene expression in the canine atrium. Since uniformity/homogeneity of gene expression is important to the eventual success of this therapy—both for optimal efficacy and to prevent the potential for pro-arrhythmia from inhomogeneous gene expression, the homogeneity of gene expression was also assessed. One of the injected genes has a V5 epitope on it, which shows up as green immunofluorescence on confocal microscopy. Gene expression (as indicated by green fluorescence) is not entirely homogeneous, in good part due to the inherent limitations of the gene injection/electroporation technique, which precludes uniform gene distribution across the atrium. The improved applicator design described herein provides more uniform gene injection+electroporation across the atria, and significantly enhances the homogeneity of gene expression in tissue (e.g., in the atrium). In some embodiments, devices are provided herein for the delivery of biologics. Such biologics may be selected from peptide, proteins, nucleic acids (e.g., DNA (e.g., plasmids, mini-genes, etc.), RNA (e.g., siRNA, shRNA, etc.), etc.), etc. In some embodiments, the device finds use in the delivery (e.g., injection) of the biologic to a tissue (e.g., cardiac tissue (e.g., atrial, ventricular, etc.), tumor tissue, renal tissue, etc.). In some embodiments, the device comprises a plurality (e.g., 4, 5, 6, 7, 8, 9, 10, 12, 14, 16, 18, 20, 25, 30, 40, 50, or more, or ranges therebetween (e.g., 8 or more)) needles (e.g., microneedles) for injection of the biologic into a tissue. In some embodiments, device herein find use in electroporating tissue to facilitate cellular uptake of the biologic. In some embodiments, a device comprises an electrode array (e.g., 2D array) or electrodes to facilitate biologic uptake across a tissue. In some embodiments, an electrode array comprises 4 or more electrodes (e.g., 4, 6, 8, 10, 12, 14, 16, 18, 20, 25, 30, 35, 40, 50, or more, or ranges therebetween (e.g., 16 or more)). In some embodiments, electrodes are regularly spaced (e.g., in rows and columns).

In some embodiments, a device applicator comprises multiple hollow micro-needles (connected to a micro-fluidic system) built into an applicator that allows homogeneous gene injection over an exposed surface of the atrium. In some embodiments, the micro-needle array is used to inject a biological therapeutic into tissue (e.g., into the epicardium or endocardium of the atrium).

In some embodiments, a device (e.g., the microneedles, electrodes, microfluidics, and other components) comprises metallic materials (e.g. stainless steel) and/or non-metallic materials (e.g. silicone).

Devices herein find use with a variety of tissues. Various tissues may be of differing thicknesses and the devices are tailored for the characteristics of the particular tissue. For example, the atrial wall is around 1-2 mm thick. In some embodiments, microneedles are selected to allow injection just under the epicardium (e.g., at a depth of 0.5 mm or less). This is akin to injecting a fluid under the skin with a needle, to raise a wheal (e.g. with a vaccine). The microneedles should therefore ideally be no more than 0.5 mm in depth. In some embodiments, needles are of any suitable diameter to minimize risk of cardiac perforation (or damage to blood vessels), yet large enough to inject DNA through these microneedles. Since DNA is viscous (especially at high concentrations), there is risk of DNA shearing if the microneedle diameter is too small.

In some embodiments, a device herein comprises and array of microneedles for the delivery of a biologic (e.g., nucleic acid). As used herein, the term "microneedle" refers to a conduit body having a base (e.g., connected to a fluidic system for delivering a biologic to the microneedle), a shaft, and a tip suitable for insertion into tissue, and has dimensions suitable for minimally invasive insertion and fluid drug formulation delivery as described herein. That is, the microneedle has a length or effective length that does not exceed 2 mm and a width (or diameter) that does not exceed 500 microns. Microneedles may be tapered, tubular, or may comprise elements of both (e.g., tubular shaft with tapered tip).

In various embodiments, the microneedle may have a length of about 50 µm to 2000 µm. In another particular embodiment, the microneedle may have a length of about 150 µm to about 1500 µm, about 300 µm to about 1250 µm, about 500 µm to about 1250 µm, about 700 µm to about 1000 µm, or about 800 to about 1000 µm. In a preferred embodiment, the length of the microneedle is about 1000 µm. In various embodiments, the proximal portion of the microneedle has a maximum width or cross-sectional dimension of about 50 µm to 500 µm, about 50 µm to about 400 µm, about 100 µm to about 400 µm, about 200 µm to about 400 µm, or about 100 µm to about 250 µm, with an aperture diameter of about 5 µm to about 400 µm. In a particular embodiment, the proximal portion of the microneedle has a maximum width or cross-sectional dimension of about 400 µm. Those skilled in the art will appreciate, however, that in embodiments in which the tip of the microneedle is beveled that the aperture diameter may be greater than the outer diameter of the proximal portion of the microneedle. The microneedle may be fabricated to have an aspect ratio (width:length) of about 1:1.5 to about 1:10. Other lengths, widths, and aspect ratios are envisioned.

A microneedle within the devices herein may comprise straight or tapered shaft. In one embodiment, the diameter of the microneedle is greatest at the base end of the microneedle and tapers to a point at the end distal the base. The microneedle may also be fabricated to have a shaft that includes both a straight (e.g., untapered) portion and a tapered (e.g., beveled) portion. The microneedles may comprise shafts that have a circular cross-section in the perpendicular, or the cross-section can be non-circular. The tip portion of the microneedles can have a variety of configurations. The tip of the microneedle can be symmetrical or asymmetrical about the longitudinal axis of the shaft. The tips may be beveled, tapered, squared-off, or rounded. In particular embodiments, the microneedle may be designed such that the tip portion of the microneedle is substantially the only portion of the microneedle inserted into the ocular tissue (e.g., the tip portion is greater than 25% of the total length of the microneedle, greater than 50% of the total length of the microneedle, greater than about 75% of the total length of the microneedle, greater than about 90% of the total length of the microneedle). In other particular embodiments, the microneedle may be designed such that the tip portion is only a portion of the microneedle that is inserted into the ocular tissue and generally has a length that is less than about 75% of the total length of the microneedle, less than about 50% of the total length of the microneedle, or less than about 25% of the total length of the microneedle. For example, in one embodiment the microneedle has a total effective length between 500 µm and 1000 µm, wherein the tip portion has a length that is less than about 400 µm, less than about 300 µm, or less than about 200 µm.

In some embodiments, a device comprises an array of microneedles. The term "microneedle array" for purposes herein refers to a two-dimensional or a three-dimensional arrangement of microneedles. The arrangement may be regular according to a repeating geometric pattern or it may be irregular. In some embodiments, a device includes an array of two or more microneedles. For example, the device may include an array of between 2 and 1000 (e.g., 2, 4, 6, 8, 10, 12, 14, 16, 18, 20, 25, 30, 35, 40, 45, 50, 60, 70, 80, 90, 100, 125, 150, 175, 200, 25, 0, 300, 350, 400, 450, 500, 600, 700, 800, 900, 1000, 1250, 1500, 1750, 2000, or ranges therebetween) microneedles. For example, in some embodiments, a device may include between 4 and 100 microneedles. An array of microneedles may include a mixture of different microneedles. For instance, an array may include microneedles having various lengths, base portion diameters, tip portion shapes, spacings between microneedles, etc.

Microneedles and arrays thereof may be formed/constructed of different biocompatible materials, including metals, glasses, semi-conductor materials, ceramics, or polymers. Examples of suitable metals include pharmaceutical grade stainless steel, gold, titanium, nickel, iron, gold, tin, chromium, copper, and alloys thereof. The polymer can be biodegradable or non-biodegradable. Examples of suitable biocompatible, biodegradable polymers include polylactides, polyglycolides, polylactide-co-glycolides (PLGA), polyanhydrides, polyorthoesters, polyetheresters, polycaprolactones, polyesteramides, poly(butyric acid), poly (valeric acid), polyurethanes and copolymers and blends thereof. Representative non-biodegradable polymers include various thermoplastics or other polymeric structural materials known in the fabrication of medical devices. Examples include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly (vinyl imidazole), chlorosulphonate polyolefins, polyethylene oxide, blends and copolymers thereof.

In some embodiments, a device comprises an applicator. In some embodiments, an applicator is a planar element that is configured to be positioned on a tissue. In some embodiments, an applicator comprises a non-conductive surface material. In some embodiments, the broad surface of the applicator contacts the surface of the tissue. In some embodiments, the applicator is flexible to facilitate continuous contact between the surfaces of the tissue and applicator. In some embodiments, the applicator houses the microneedles and electrode array. In some embodiments, placement of the applicator on the surface of a tissue places the microneedles and electrodes in proper contact with the tissue.

In some embodiments, an applicator is made from a flexible material that will allow greater coverage of the exposed surface of a tissue (e.g., a single atrium (e.g. left atrial free wall, posterior left atrium, left atrial appendage)). For example, dimensions of a typical exposed atrial surface (in a human) are around 2-4 cm×3-5 cm (typical atrial volume is 22-58 ml). In some embodiments, an applicator is designed to approximate those dimensions (e.g., 1-10 cm (e.g., 1, 2, 3, 4, 5, 6, 7, 8, 9, 10)×1-10 (e.g., 1, 2, 3, 4, 5, 6, 7, 8, 9, 10) cm). An exemplary device was produced (See e.g., FIG. 2) that is approximately 2 cm×7 cm, with seven electroporation electrodes (e.g., 6 bipoles).

In some embodiments, the microneedles and electrodes of a device herein a presented on the surface of the applicator in any suitable orientation. For example, in some embodiments, a plurality of electrodes (e.g., 4, 6, 8, 10, or more) are spaced along one dimension of the applicator, and one or more microneedles (e.g., 1, 2, 5, 10, or more) are positioned between pairs of electrodes. In some embodiments, an array of electrodes presents a two-dimensional grid of electrodes, which microneedles spaced (e.g., regularly) within the array. Any suitable orientation and arrangement of microneedles and electrodes on the surface of an applicator is within the scope herein.

In some embodiments, an applicator presents microneedles to the tissue such that the microneedles are oriented directly into the tissue (e.g., 90° or perpendicular to the tissue). In some embodiments, the applicator presents the microneedles at an angle (e.g., 5-90°) with respect to the tissue surface. Any suitable microneedle angle is within the scope herein (e.g., 5°, 10°, 15°, 20°, 25°, 30°, 35°, 40°, 45°, 50°, 55°, 60°, 65°, 70°, 75°, 80°, 85°, 90°, and ranges therebetween (e.g., 30° to 75°). Experiments conducted during development of embodiments herein indicate that a shallower injection angle (e.g., <90°, <80°, <70°, <60°, <50°, <40°, <30°, <20°, <10°) facilitates the creation of a 'bleb' (e.g., a bubble liquid) of the injected media just beneath the surface of the tissue. In some embodiments, the formation of a bleb of injected material is desired. In the case of thin tissues (e.g., in the atrium), a shallower injection angle (e.g., <90°, <80°, <70°, <60°, <50°, <40°, <30°, <20°, <10°) reduces the probability puncturing through the tissue. In some embodiments, a shallower injection angle (e.g., <90°, <80°, <70°, <60°, <50°, <40°, <30°, <20°, <10°) delivers the injectable away from the needle tip upon injection, thus reducing the likelihood of it leaking out upon retraction of the microneedle.

To achieve homogeneous coverage of tissue area (e.g., both atria) spacing of injection needles is optimized (e.g., 0.25-5 mm spacing between injection needles (e.g., 0.25, 0.3, 0.4, 0.5, 0.6, 0.7, 0.8, 0.9, 1, 1.5, 2, 2.5, 3, 3.5, 4, 4.5, 5)).

In some embodiments, a delivery device incorporates multiple electroporation electrodes (e.g., with 0.5 to 2 cm inter-electrode spacing) built into the applicator to facilitate simultaneous and uniform electroporation over the entire exposed tissue surface (e.g., atrial surface). In some embodiments, a device comprises an electroporation electrode array and associated electronic circuitry that allows simultaneous electroporation through at least 6 (e.g., 6, 7, 8, 9, 10, 12, 14, 16, 18, 20, 25, 30, or more) bipolar, evenly space electroporation electrodes.

In some embodiments, a device herein comprises an electroporation system comprising an electrode array and one or more of: an energy source, an electroporation generator, an electroporation controller (e.g., to determine the amount of electroporation energy delivered to each electrode of the array and the timing of such delivery), and any wiring connecting such elements. In some embodiments, the electroporation system (e.g., energy source, electroporation generator and/or electroporation controller, etc.) is configured to selectively energize the electrodes at desired energies and at desired times. In some embodiments, all electrodes are simultaneously energized. In some embodiments, a portion of the electrodes are simultaneously energized. In some embodiments, adjacent electrodes are energized in a bipolar fashion to produce a local electric field between the electrode. In some embodiments, the energizing of electrodes is coordinated with the delivery of therapeutic by microneedles between selected electrodes. For example, a set of microneedles are injected into the tissue, the microfluidic system delivers therapeutic through the injected microneedles, and electrodes adjacent to the microneedles are energized to facilitate electroporation in a coordinated manner. In some embodiments, injection, therapeutic delivery, and electroporation are performed simultaneously for a subset of the microneedles/electrodes in an array. In some embodiments, injection, therapeutic delivery, and electroporation are in ordered (timed) steps for a subset of the microneedles/electrodes in an array. In some embodiments, injection, therapeutic delivery, and electroporation are performed simultaneously for all the microneedles/electrodes in an array. In some embodiments, injection, therapeutic delivery, and electroporation are in ordered (timed) steps for all the microneedles/electrodes in an array.

In some embodiments, provided herein are catheters comprising the systems and devices described herein. In some embodiments, the distal end of the catheter is placed at a treatment site. In some embodiments, the distal end of the catheter comprises an applicator, microneedles, and electroporation arrays described herein. In some embodiments, an applicator, microneedles, and electroporation array are contained within the catheter and deployed from the distal end of the catheter at the treatment site.

In some embodiments, a fluidic system facilitates delivery (e.g., timed delivery, coordinated delivery, etc.) of therapeutic to the treatment site via the set of microneedles on the applicator. In some embodiments, therapeutic is delivered through all of the microneedles concurrently. In some embodiments, the therapeutic is delivered through a subset (e.g., 1, 2, 5, 10, etc.) of the microneedles at one timepoint, and other subset(s) of microneedles at a second (third, fourth, fifth, etc.) timepoint (e.g., spaced by 0.5 seconds, 1 second, 2 seconds, 3 seconds, 4 seconds, 5 seconds, 10 seconds, 20 seconds, 30 seconds, 45 seconds, 1 minute, 2 minutes, 5 minutes, or more or ranges therebetween). In some embodiments, the fluidic system delivers the therapeutic from a source at or near the proximal end of the catheter to the microneedles at the distal end of the catheter.

In some embodiments, an electroporation system facilitates energy delivery (e.g., timed delivery, coordinated delivery, etc.) to the treatment site via the electrodes of the electrode array. In some embodiments, all of the electrodes are energized concurrently. In some embodiments, a subset (e.g., 2, 4, 5, 7, 9, 10, 16, etc.) of the electrodes are energized at one timepoint, and other subset(s) of electrodes are energized at a second (third, fourth, fifth, etc.) timepoint (e.g., spaced by 0.5 seconds, 1 second, 2 seconds, 3 seconds, 4 seconds, 5 seconds, 10 seconds, 20 seconds, 30 seconds, 45 seconds, 1 minute, 2 minutes, 5 minutes, or more or ranges therebetween). In some embodiments, the electroporation system connects an energy source at or near the proximal end of the catheter (e.g., electroporation generator, electroporation controller, etc.) to the microneedles at the distal end of the catheter.

In some embodiments, devices and method are provided for the delivery of biological agents to the atrium for treating AF. Those biologics may be the gene described herein, other genes, other nucleic acid-based treatments, or other non-nucleic acid biologics (e.g., peptide, stem cells, etc.). In other embodiments, devices and methods are provided for the delivery of biological therapeutics to the cardiac ventricle, e.g. for the treatment of congestive heart failure, myocardial infarction, ventricular arrhythmias. In some embodiments, biologics are delivered to other organs, e.g. skin, liver, lungs, etc.

In some embodiments, devices herein find use in irreversible electroporation to treat tumors etc. High energy electroporation has been used to treat malignancies in some organs e.g. liver. Since the goal of electroporation in these circumstances is to kill tumor cells, the electroporation energy used in such applications far exceeds that used for gene delivery (e.g., to the atrium). However, in some embodiments, the devices herein find use in the treatment of tumors by applying higher energies over a wide surface area (e.g., without being used to deliver a biological agent).

U.S. patent application Ser. Nos. 12/959,864 and 13/080,755 (herein incorporated by reference in their entireties) describe biologic delivery and electroporation devices, the features of which may find use in embodiments herein.

REFERENCES

The following references, some of which are cited above by number, as herein incorporated by reference in their entireties.
1. Benjamin E J, Levy D, Vaziri S M, D'Agostino R B, Belanger A J and Wolf P A. Independent risk factors for atrial fibrillation in a population-based cohort. The Framingham Heart Study. JAMA. 1994; 271:840-4.
2. Balasubramaniam R and Kistler P M. AF and Heart failure: the chicken or the egg?. Heart. 2009; 95:535-539.
3. Feinberg W M, Blackshear J L, Laupacis A, Kronmal R and Hart R G. Prevalence, age distribution, and gender of patients with atrial fibrillation. Analysis and implications. Archives of Internal Medicine. 1995; 155:469-73.
4. Lakshminarayan K, Anderson D C, Herzog C A and Qureshi A I. Clinical epidemiology of atrial fibrillation and related cerebrovascular events in the United States. Neurologist. 2008; 14:143-50.
5. Lip G Y, Kakar P and Watson T. Atrial fibrillation—the growing epidemic.[comment]. Heart. 2007; 93:542-3.
6. Ling L H, Kistler P M, Kalman J M, Schilling R J and Hunter R J. Comorbidity of atrial fibrillation and heart failure. Nat Rev Cardiol. 2016; 13:131-47.
7. Gerstenfeld E P, Sauer W, Callans D J, Dixit S, Lin D, Russo A M, Beldner S, McKernan M and Marchlinski F E. Predictors of success after selective pulmonary vein isolation of arrhythmogenic pulmonary veins for treatment of atrial fibrillation. Heart Rhythm. 2006; 3:165-70.
8. Pappone C, Oral H, Santinelli V, Vicedomini G, Lang C C, Manguso F, Torracca L, Benussi S, Alfieri O, Hong R, Lau W, Hirata K, Shikuma N, Hall B and Morady F. Atrio-esophageal fistula as a complication of percutaneous transcatheter ablation of atrial fibrillation. Circulation. 2004; 109:2724-6.
9. Calkins H, Kuck K H, Cappato R, Brugada J, Camm A J, Chen S A, Crijns H J, Damiano R J, Jr., Davies D W, DiMarco J, Edgerton J, Ellenbogen K, Ezekowitz M D, Haines D E, Haissaguerre M, Hindricks G, Iesaka Y, Jackman W, Jalife J, Jais P, Kalman J, Keane D, Kim Y H, Kirchhof P, Klein G, Kottkamp H, Kumagai K, Lindsay B D, Mansour M, Marchlinski F E, McCarthy P M, Mont J L, Morady F, Nademanee K, Nakagawa H, Natale A, Nattel S, Packer D L, Pappone C, Prystowsky E, Raviele A, Reddy V, Ruskin J N, Shemin R J, Tsao H M and Wilber D. 2012 HRS/EHRA/ECAS Expert Consensus Statement on Catheter and Surgical Ablation of Atrial Fibrillation: recommendations for patient selection, procedural techniques, patient management and follow-up, definitions, endpoints, and research trial design. Europace. 2012; 14:528-606.
10. Verma A, Patel D, Famy T, Martin D O, Burkhardt J D, Elayi S C, Lakkireddy D, Wazni O, Cummings J, Schweikert R A, Saliba W, Tchou P J and Natale A. Efficacy of adjuvant anterior left atrial ablation during intracardiac echocardiography-guided pulmonary vein antrum isolation for atrial fibrillation. J Cardiovasc Electrophysiol. 2007; 18:151-6.
11. Rodrigues A C, Scannavacca M I, Caldas M A, Hotta V T, Pisani C, Sosa E A and Mathias W, Jr. Left atrial function after ablation for paroxysmal atrial fibrillation. American Journal of Cardiology. 2009; 103:395-8.
12. Aistrup G L, Cokic I, Ng J, Gordon D, Koduri H, Browne S, Arapi D, Segon Y, Goldstein J, Angulo A, Wasserstrom J A, Goldberger J J, Kadish A H and Arora R. Targeted nonviral gene-based inhibition of Galpha(i/o)-mediated vagal signaling in the posterior left atrium decreases vagal-induced atrial fibrillation. Heart Rhythm. 2011; 8:1722-9.
13. Greener I and Donahue J K. Gene therapy strategies for cardiac electrical dysfunction. J Mol Cell Cardiol. 2011; 50:759-65.
14. Korantzopoulos P, Kolettis T M, Galaris D and Goudevenos J A. The role of oxidative stress in the pathogenesis and perpetuation of atrial fibrillation. Int J Cardiol. 2007; 115:135-43.
15. Youn J Y, Zhang J, Zhang Y, Chen H, Liu D, Ping P, Weiss J N and Cai H. Oxidative stress in atrial fibrillation: an emerging role of NADPH oxidase. J Mol Cell Cardiol. 2013; 62:72-9.
16. Jeong E M, Liu M, Sturdy M, Gao G, Varghese S T, Sovari A A and Dudley S C, Jr. Metabolic stress, reactive oxygen species, and arrhythmia. J Mol Cell Cardiol. 2012; 52:454-63.
17. Su C H, Wu Y J, Wang H H and Yeh H I. Nonviral gene therapy targeting cardiovascular system. Am J Physiol Heart Circ Physiol. 2012; 303:H629-38.
18. Dean D A. Nonviral gene transfer to skeletal, smooth, and cardiac muscle in living animals. Am J Physiol Cell Physiol. 2005; 289:C233-45.
19. Tevaearai H T, Gazdhar A, Giraud M N and Fluck M. In vivo electroporation-mediated gene delivery to the beating heart. Methods Mol Biol. 2014; 1121:223-9.
20. Rincon M Y, VandenDriessche T and Chuah M K. Gene therapy for cardiovascular disease: advances in vector development, targeting, and delivery for clinical translation. Cardiovasc Res. 2015; 108:4-20.

The invention claimed is:

1. A device comprising:
   (a) a planar applicator comprising a surface configured to contact a tissue surface, wherein the planar applicator is flexible to facilitate continuous contact between the surface of the planar applicator and the tissue surface;
   (b) an electroporation array for coordinated delivery of uniform electroporation energy to the tissue surface, the electroporation array comprising 6 or more bipolar electroporation electrodes evenly spaced along the surface of the planar applicator; and
   (c) a microneedle array comprising two or more microneedles located on the surface of the planar applicator between each adjacent pair of electroporation electrodes;
   wherein the planar applicator presents (i) the microneedle array and (ii) the electroporation array for simultaneously contacting the tissue surface;
   wherein microneedles of the microneedle array and electrodes of the electroporation array are capable of simultaneously delivering a fluid biologic and electroporation energy to the tissue.

2. The device of claim 1, wherein the planar applicator is located at a distal end of a catheter.

3. The device of claim 1, wherein the microneedle array comprises 200 or fewer microneedles.

4. The device of claim 1, wherein the electroporation array comprises 6 to 200 electrodes.

5. The device of claim 1, wherein the planar applicator is configured to cover a portion of the tissue that is 2-20 $cm^2$.

6. The device of claim 1, wherein the electronic system comprises an electroporation controller and an electroporation generator.

7. The device of claim 6, wherein the electroporation controller activates all or a subset of the electrodes in the electroporation array according to a programed schedule.

8. The device of claim 1, wherein when the surface of the planar applicator is in proper contact with the tissue surface, the microneedles are at an angle between 5° and 90° to the tissue surface.

9. A method of delivering a biologic agent to a tissue, comprising:
   (a) placing the surface of the planar applicator of the device of claim 1 against the tissue surface;
   (b) injecting the biologic agent into the tissue via the microneedle array; and
   (c) electroporating the tissue with the electroporation array.

10. The method of claim 9, wherein the tissue is cardiac tissue.

11. The method of claim 10, wherein the tissue comprises epicardial tissue.

12. The method of claim 10, wherein the tissue comprises endocardial tissue.

13. The method of claim 9, wherein electroporation by all or a portion of the electroporation array is coordinated with delivery of the biologic agent into the tissue by all or a subset of the microneedle array.

14. The method of claim 13, wherein the all or the portion of the electroporation array is energized in a coordinated manner with delivery of the biologic agent by all of the portion of the microneedle array.

15. The method of claim 13, wherein the all or the portion of the electroporation array is energized immediately before, during, and/or immediately after delivery of the biologic agent by all or a portion of the microneedle array.

16. The method of claim 13, wherein different portions of the microneedle array and different portions of the electroporation array are utilized at different times in a treatment course.

* * * * *